United States Patent
Bilitz et al.

[19]

[11] Patent Number: 5,980,511
[45] Date of Patent: Nov. 9, 1999

[54] MEDICAL INSTRUMENT HANDLE WITH INTEGRAL PALM BLOCKING MEMBER

[75] Inventors: Mark R. Bilitz, Minneapolis, Minn.; Theodor Esser, Stony Brook, N.Y.

[73] Assignee: T. Esser, Stony Brook, N.Y.

[21] Appl. No.: 09/079,483

[22] Filed: May 15, 1998

[51] Int. Cl.$^6$ .................................................. A61B 17/00
[52] U.S. Cl. .................................................................. 606/1
[58] Field of Search ................................. 600/131, 146; 606/1, 205, 206, 207, 174; D24/133, 143, 144, 145, 146, 147, 148, 149

[56] References Cited

U.S. PATENT DOCUMENTS

| | | |
|---|---|---|
| H1028 | 3/1992 | Falke et al. . |
| D. 345,212 | 3/1994 | Brancel et al. . |
| D. 362,504 | 9/1995 | Younker et al. . |
| D. 385,627 | 10/1997 | Cook et al. . |
| 4,815,476 | 3/1989 | Clossick . |
| 4,887,612 | 12/1989 | Esser et al. . |
| 4,896,678 | 1/1990 | Ogawa . |
| 5,094,247 | 3/1992 | Hernandez et al. . |
| 5,133,727 | 7/1992 | Bales et al. . |
| 5,146,928 | 9/1992 | Esser . |
| 5,147,380 | 9/1992 | Hernandez . |
| 5,184,625 | 2/1993 | Cottone et al. . |
| 5,238,002 | 8/1993 | Devlin et al. . |
| 5,250,073 | 10/1993 | Cottone et al. . |
| 5,251,638 | 10/1993 | Cottone et al. . |
| 5,286,255 | 2/1994 | Weber . |
| 5,308,357 | 5/1994 | Lichtman . |
| 5,389,104 | 2/1995 | Hahnen et al. . |
| 5,395,375 | 3/1995 | Turkel et al. . |
| 5,439,461 | 8/1995 | Storz . |
| 5,451,227 | 9/1995 | Michaelson . |
| 5,522,830 | 6/1996 | Aranyi . |
| 5,620,415 | 4/1997 | Lucey et al. . |
| 5,643,248 | 7/1997 | Yoon . |
| 5,666,965 | 9/1997 | Bales et al. . |
| 5,683,412 | 11/1997 | Scarfone . |
| 5,735,873 | 4/1998 | MacLean . |

*Primary Examiner*—John P. Leubecker

[57] ABSTRACT

A medical instrument handle consisting of an ergonomic main handle body incorporating an integral palm blocking arch which will provide a simple and reliable means for preventing the application of palm pressure to the thumb ring of the actuator by the operator, while concurrently making it considerably more ergonomic, smooth and reliable in operation, and less expensive to produce.

7 Claims, 4 Drawing Sheets

MEDICAL INSTRUMENT HANDLE WITH INTEGRAL PALM BLOCKING MEMBER

BACKGROUND—FIELD OF INVENTION

This invention relates to medical instruments, specifically to an improved handle for medical instruments.

BACKGROUND—DESCRIPTION OF PRIOR ART

For purposes herein, the distal end of a medical instrument handle or any part thereof, is the end closest to the surgical site and distant from the surgeon, while the proximal end of the medical instrument handle is the end most proximate the surgeon and distant the surgical site.

The prior art discloses numerous handle configurations for medical instruments. For example, in the field of endoscopy and arthroscopy, typical handle types include a type of handle commonly known as the spool-type handle. Generally, such handles consist of a spool-shaped grasping member with a bore through which a shaft member with an attached thumb ring is slidably mounted. The construction of such handles permits for displacement of the members relative to each other, which motion is then transmitted to an end effector, for example opening and closing biopsy forceps jaws.

Another type of handle is the scissors-type grip, variants of which are commonly found on "rigid tube and push rod" type endoscopic instruments.

Yet another grasping arrangement is the so-called syringe-type handle, which generally consists of a figure-eight shaped grasping member with finger placements slidably mounted on or to a handle portion which receives the thumb. Again, the parts are typically displaceable relative to each other, and this motion is transmitted to an end effector. The syringe-type handle is commonly employed on instruments with end effectors actuated by drive wires.

A patient undergoing a surgical procedure faces risks both known and unknown. The level of risk increases significantly when medical personnel perform procedures for the first time. Similarly, operative risk increases when surgeons use unfamiliar instruments and equipment. Furthermore, even those surgeons or surgical assistants well versed in operative methods and proper use of equipment may on occasion inadvertently depart from their routines. In the case of surgeons performing particularly delicate procedures such as arthroscopies or tissue biopsies, the risk factor is increased.

One obvious way to minimize operative risk is to provide foolproof medical instruments. In the absence of such devices the danger exists that, for example, a surgeon may inadvertently apply abrupt and excessive force to an instrument's handle or grip. A surgeon could conceivably apply excessive force intentionally as well as inadvertently, perhaps under the mistaken belief that applying greater force or leverage to an instrument would lead to more positive grasping, cutting or other manipulation of tissue. In fact, situations have occurred in which a physician has thrust the heel or palm of a free hand against the thumb ring of a biopsy forceps in the hope of achieving a more precise cut and better tissue sample. The resultant stress on the end effectors of the often delicate and fragile end effectors of endoscopic instruments has in the past resulted in material failure. Patients' lives have been endangered as the end effectors shattered, leaving sharp metal fragments inside the patient's body cavities.

Many basic and widely used types of medical instrument handles have no means for preventing the operator from applying excessive force to the instrument. Some manufacturers, having recognized this problem, have imprinted product packaging with warning labels emphasizing proper instrument grasping and use, and the dangers inherent in improper handling. Others have attempted to provide some basic means of intervention to improper operation, such as the placement of stop pins to limit handle component travel. Still others have developed complex force limiting arrangements employing "break away," or frangible, links and control members. Many devices employ ratchet mechanisms, springs and similar components intended to reduce force as it is applied to the instrument handle.

Unfortunately, the existing designs for reducing or limiting force are often inadequate. Intensive design work increasingly results in unnecessarily complicated medical instrument handles. These are generally neither comfortable nor ergonomic. Also, they are replete with sensitive components, making them difficult to sterilize and expensive to manufacture.

Clossick U.S. Pat. No. 4,815,476 (March/1989) discloses an endoscopic biopsy forceps with a locking handle. The handle portion of the invention is of the syringe type, and has in practice been found somewhat uncomfortable to many physicians. The invention is unsuitable in that it offers no means for preventing the application of excessive force, in particular the force which may result from the application of the palm or heel of the operator's open free hand to the thumb ring of the instrument's handle.

Bales et al. U.S. Pat. No. 5,133,727 (July/1992) discloses a radial jaw biopsy forceps device incorporating a typical spool-type handle. Significantly, the packaging for this device bears a note of caution advising medical personnel as to proper use, and specifically warning that improper operation, such as pushing on the thumb ring with the palm of one's hand may result in force so excessive as to cause end effector damage. The device offers no means of preventing the operator from exerting palm pressure on the thumb ring.

Cottone et al. U.S. Pat. No. 5,184,625 (February/1993) discloses a biopsy forceps device having an improved handle said to be ergonomic and suitable for ambidextrous use. The handle is of complex construction, incorporating a multiplicity of linkages to connect the squeezable trigger member to a drive wire, and is expensive to manufacture due to its complexity. Moreover, the device is susceptible to the rigors of sterilization. Finally, the device offers no clear means for preventing the exertion of excessive force.

Devlin et al. U.S. Pat. No. 5,238,002 (August/1993) discloses a disposable biopsy forceps device, the handle portion of which is a typical syringe type, and which offers no means for preventing the application of palm pressure to the thumb ring.

Cottone et al. U.S. Pat. No. 5,251,638 (October/1993) discloses a biopsy forceps device having an improved handle assembly of the scissors type. The handle portion is of complicated construction, and the many components thereof make the handle expensive to manufacture and prone to damage during sterilization. The device has no means for preventing the operator from applying excessive manual force.

Younker et al. U.S. Pat. No. D 362,504 (September/1995) discloses a scissors-type handle portion for an endoscopic instrument. This handle configuration is unsuitable for ambidextrous use, and does not appear to offer any means for preventing the operator from seizing the finger rings in such as way as to apply excessive force.

Yoon U.S. Pat. No. 5,643,248 (July/1997) discloses a medical instrument with a force limiting mechanism. The device is of the rigid tube and push rod type, and employs a complex force limiting mechanism including spring biasing and ratcheting mechanisms. The device is complex, involving numerous components, and is expensive to manufacture, unsuitable for drive wire actuated medical instruments, and poses potential problems in terms of being susceptible to damage during sterilization.

Cook et al. U.S. Pat. No. D 385,627 (October/1997) discloses a syringe-type medical instrument handle with no identifiable means for preventing the application of palm pressure to the thumb ring of the handle.

Scarfone U.S. Pat. No. 5,638,412 (November/1997) discloses a force limiting member for endoscopic instruments and instruments incorporating same. The force limiting member consists of a drive wire which at its proximal end incorporates a pre-stressed spring element designed to limit the amount of force which may be applied to the end effectors to that pressure which can normally be generated by the human hand. The invention is presented with two alternate handle configurations, one variant being a spool type handle incorporating the spring mechanism. A stop pin is proposed to limit the actuator's range of travel, but such a stop pin may easily be overcome by the pressure exerted by an open hand against the instrument's thumb ring. The other handle configuration presented in the drawing figures is a complex handle assembly consisting of two clamshell-like halves. These enclose a multiplicity of complex linkage elements and pivots which transmit leverage from a squeezable trigger. This device is complex and costly to manufacture, as well as being susceptible to damage during sterilization. The high manufacturing cost of such a device necessitates repeated reuse to make it economical.

Further types of force limiting medical instruments and force limiting handles for medical instruments exist. All employ combinations of complex frangible links, frangible actuating members, springs and levers to limit the amount of force which can be applied to the end effectors. Ogawa U.S. Pat. No. 4,896,678 (January/1990) discloses a frangible link push rod arrangement. Falk et al. U.S. Statutory Invention registration No. H1,208 (March/1992) discloses an endoscopic instrument having a handle with a frangible actuating member. Weber U.S. Pat. No. 5,286,255 (February/1994) discloses a complicated force limiting arrangement of levers and compression springs in the handle of a rigid tube and push rod type surgical forceps. Hahnen et al. U.S. Pat. No. 5,389,103 (February/1995) discloses an arthroscopic surgical instrument with a frangible push rod. The constructions in these inventions typically employ complex frangible links or springs, which render the devices complex and expensive. Moreover, the initial cost of such complex instruments is high, requiring potentially risky reuse to make the acquisition of such devices cost effective.

OBJECTS AND ADVANTAGES

Accordingly, it is an object of the present invention to provide a novel medical instrument handle which is ergonomic, with a positive grip, light in weight, of simple construction, low in cost, and reliable in operation.

It is another object of the present invention to provide a medical instrument handle of the type described herein which incorporates a simple structural element for preventing the application of excessive manual pressure exerted upon the instrument by the heel or palm of the operator's open hand, thereby preventing damage to the end effectors of a drive wire actuated medical instrument.

It is yet another object of the present invention to provide a medical instrument handle of the type described herein, in which the device eliminates complex force limiting mechanisms such as frangible links and springs and renders the construction thereof extremely simple with as few as possible operating components.

Although applicable a wide range of medical instrumentation, the present invention lends itself in particular to drive wire actuated endoscopic instruments such as biopsy forceps, tissue snares, and cytology brushes, and presents an ergonomic handle suitable for ambidextrous use. The handle overcomes the need for complex and costly force limiting mechanisms by means of a simple handle design which incorporates an integral palm blocking arch which in the preferred embodiment effectively limits the surgeon or assistant to using the thumb alone to guide and drive the actuating member, and prevents the user from applying palm pressure to the thumb ring. Still further objects and advantages will become apparent from a consideration of the ensuing description and accompanying drawings.

DRAWING FIGURES

Figure 1:
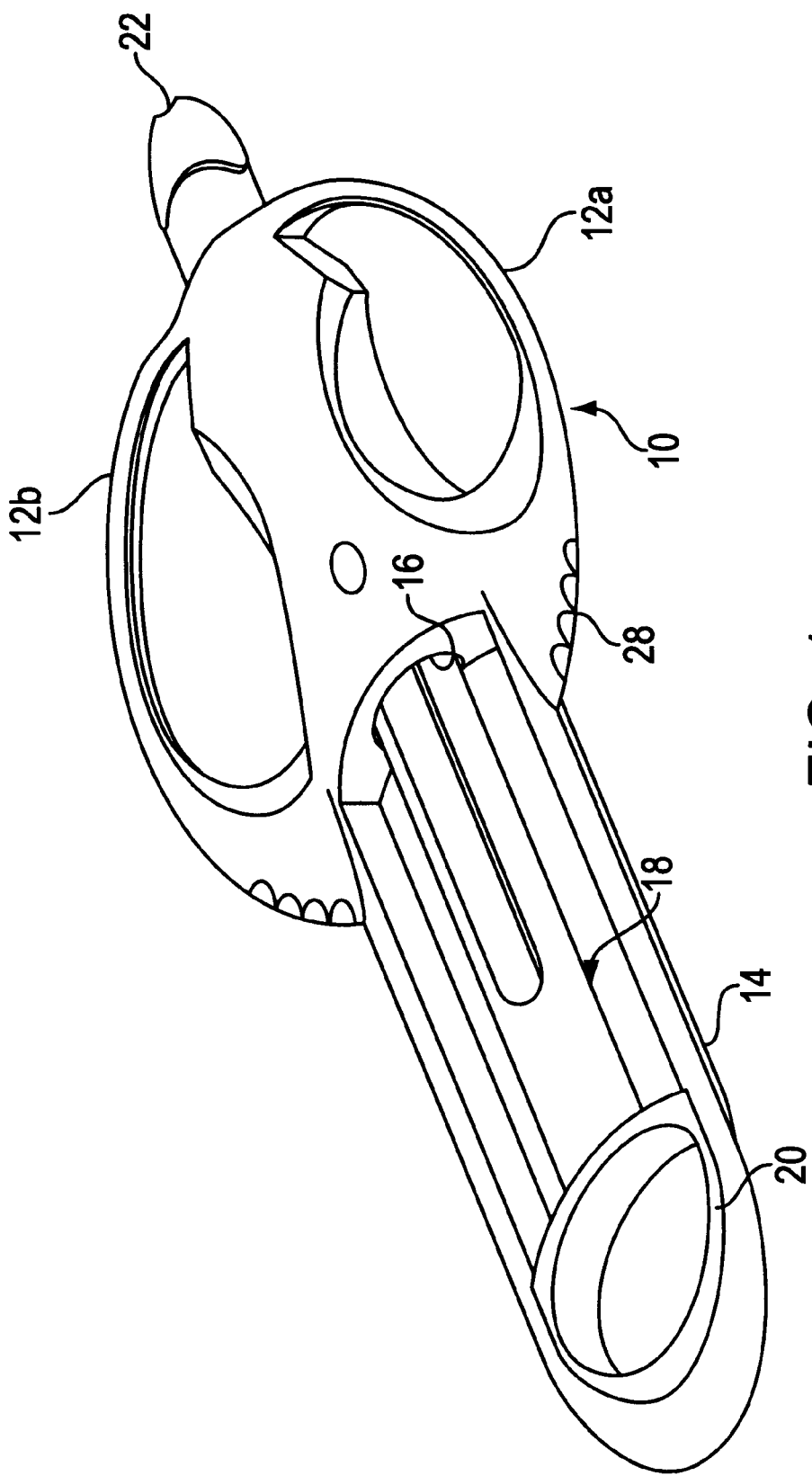
FIG. 1 is a perspective view of a medical instrument handle constructed in accordance with the present invention.

REFERENCE NUMERALS IN DRAWINGS 10 main handle body
12a finger ring
12b finger ring
14 palm blocking arch
16 channel
18 actuator
20 thumb ring
22 lumen
24 assembly hole
26 assembly hole plug
28 ridges
30 flanges
32 slot

SUMMARY

In accordance with the present invention an improved medical instrument handle comprises an ergonomic main handle body with an integral palm blocking arch at its proximal end and contoured finger grasping points at its distal end, and slidably mounted to the main handle body a thumb engaging member to which may be connected an end effector driver.

DESCRIPTION—FIGS. 1 TO 4

As shown in FIG. 1, a typical embodiment of the present invention comprises a main medical instrument handle body or main handle body 10 and related components. In the preferred embodiment the main handle body 10 is formed of an injection molded thermoplastic such as polyethylene or polycarbonate. The main handle body 10 consists of symmetrically opposed grasping points or finger rings 12a and 12b located at its distal end, and integral palm blocking arch 14 at its proximal end, and lumen or channel 16, which is oval in cross section and which is located medially between finger rings 12a and 12b. Channel 16 receives the thumb ring triggering member or actuator 18, which in the preferred embodiment is also formed of injection molded thermoplastic, and which is comprised of a shaft integrally joined with thumb grasping ring or thumb ring 20 at its proximal end, and a lumen 22 at its distal end into which may be inserted the proximal terminus of the instrument end effector drive wire or drive wires (not shown). As assembly hole 24 permits for the attachment of instrument end effector drive wire or drive wires to a fixed point inside channel 16. Ridges 28 are for decorative purposes only.

Figure 2:
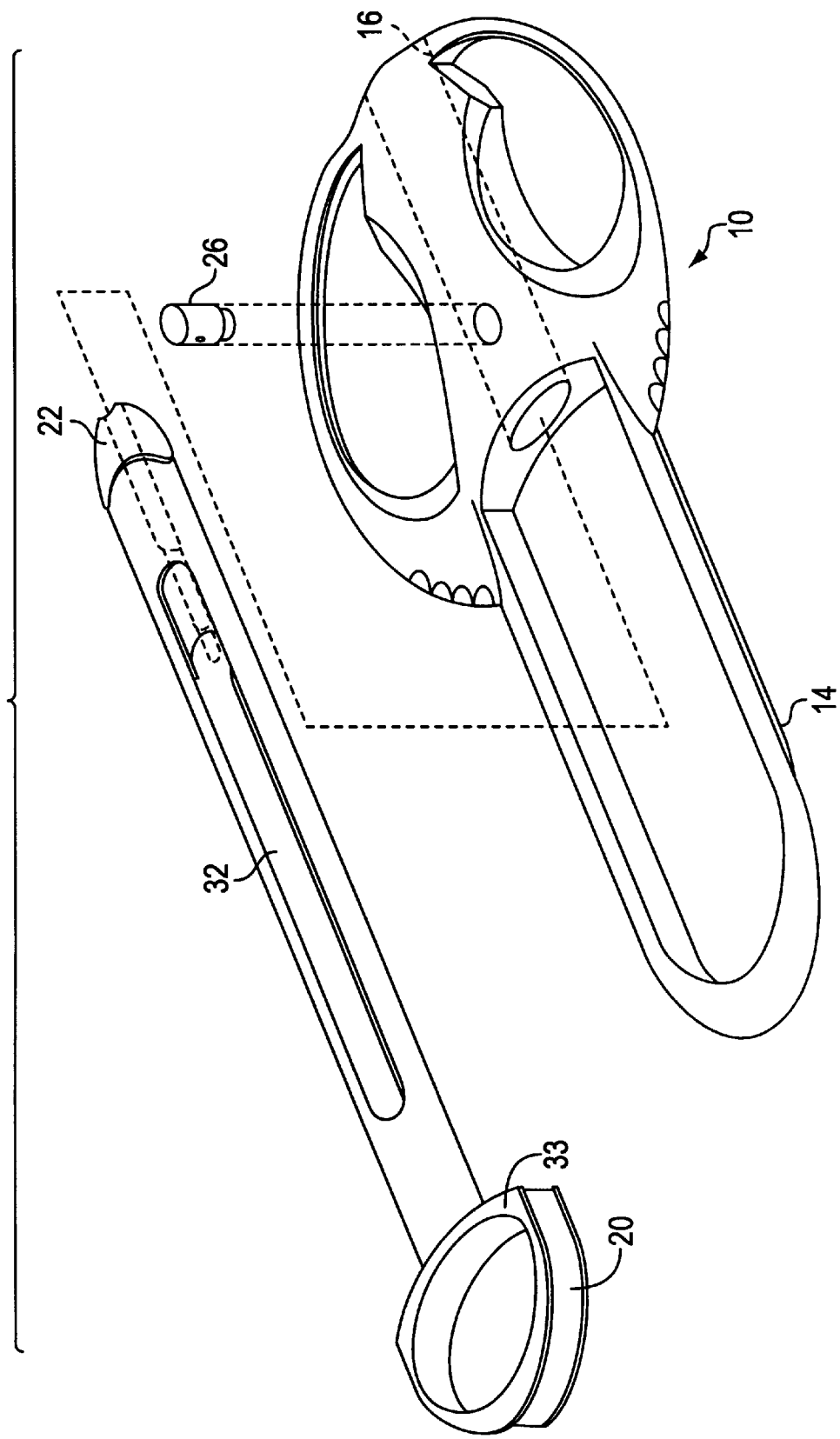
FIG. 2 is an exploded view of the present invention showing various of the components employed in the embodiment illustrated in FIG. 1.

FIG. 2 shows an exploded view of the instrument disclosed in FIG. 1. The locations of channel 16 and lumen 22 are indicated by broken lines. Also shown is an assembly hole plug 26, which in the preferred embodiment is formed of injection molded thermoplastic, and which is inserted into assembly hole 24 and then pressed flush with main handle body 10, sealing assembly hole 24 after final connection of instrument end effector drive wire or wires. Also shown in greater detail is slot 32 which permits for reciprocating slidable motion of actuator 18 about an anchoring point (not shown) for a drive wire or drive wires (not shown). Further shown in greater detail are flanges 30 of integral thumb ring 20 of actuator 18.

Figure 3:
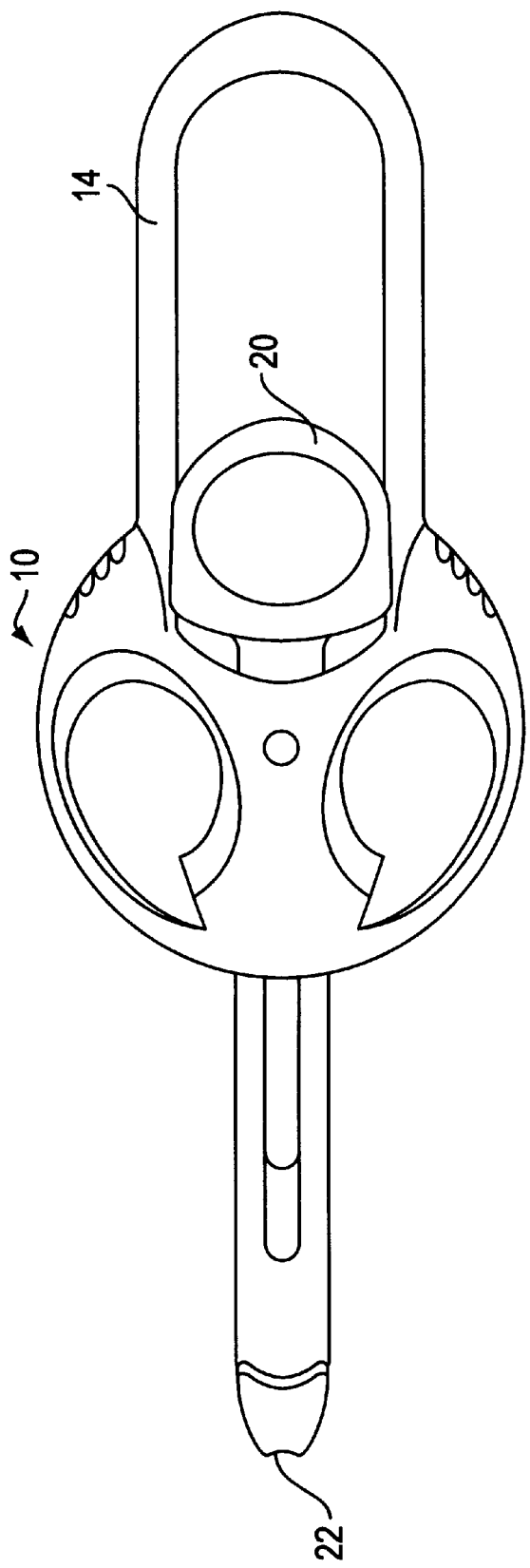
FIG. 3 is a plan view of the present invention as shown in FIGS. 1 and 2 with the handle in an end effector retracted position.
Figure 4:
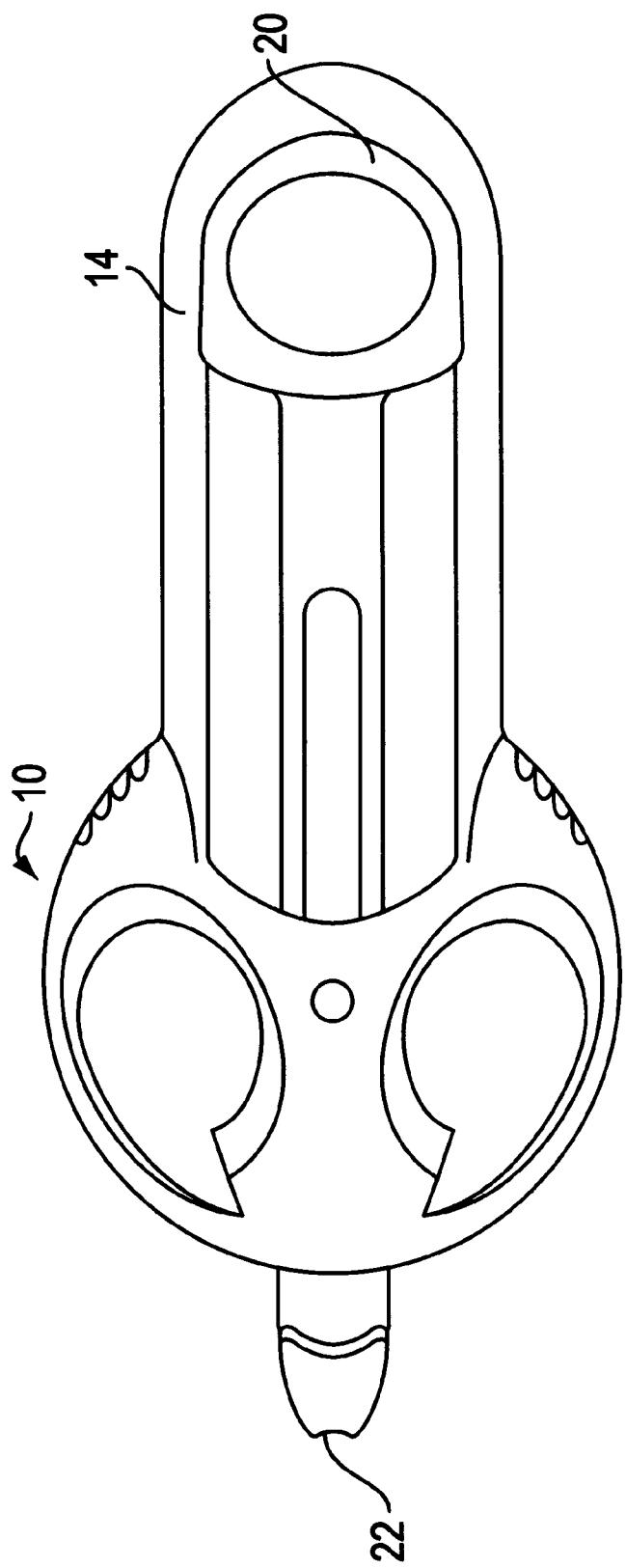
FIG. 4 is an illustration similar to FIG. 3 with the invention in an end effector extended position.

FIGS. 3 and 4 respectively show the inventive device in end effector retracted and extended positions.

From the description above, a number of advantages of the invention become evident:

(a) a medical instrument handle is provided which is suitable for a wide variety of drive wire actuated medical instruments, and which is ergonomic, simply made, and reliable;

(b) a medical instrument handle is provided which by means of a simple structural element, an integral palm blocking arch, prevents the operator from applying excessive and possibly damaging force via the heel or palm of the operator's free hand;

(c) a medical instrument handle is provided which eliminates the need for complex force limiting arrangements such as springs, frangible links, and the like;

(d) a medical instrument handle is provided which is inexpensive and may be incorporated into a similarly inexpensive, disposable or multi-use instrument.

Operation—FIGS. 1 to 4

Operation and use of the handle arrangement of the invention is simple and straightforward.

The operator inserts the second and middle fingers of one hand into finger rings 12a and 12b, and the thumb of the same hand into thumb ring 20. As the thumb is moved back and forth, actuator 18 slidably reciprocates, and the instrument end effector drive wire or wires fixed in place move relative to actuator 18.

As shown in all Figs., palm blocking arch 14 serves as a guide for actuator 18 by providing in effect rails for flanges 30 of thumb ring 20 of actuator 18. Flanges 30 slightly overlap palm blocking arch 14 and are guided by it, ensuring straight and smooth motion.

Most importantly, palm blocking arch 14 serves as a barrier to the application of force from the heel or palm of the operator's free hand by making it physically impossible to manipulate thumb ring 20 of actuator 18 with anything other than the operator's thumb.

Conclusions, Ramifications, and Scope

It is seen that according to the invention, a medical instrument handle is provided which is ergonomic and which offers the following advantages:

(a) the elimination of the problem of an operator exerting excessive palm pressure to the thumb ring of a medical instrument handle, and ultimately to the end effectors of a medical instrument;

(b) the elimination of any danger to a patient caused by the accidental breakage of an end effector resulting in the possibility of end effector fragments lodging in the patient's body cavity;

(c) the problem of operator fatigue is diminished as the medical instrument handle is light in weight, suitable for ambidextrous use, and provides a positive grip;

(d) the production cost of the medical instrument handle is considerably reduced due to the considerably fewer employed components and articulated parts, thereby also increasing its operation reliability and stability, and also increasing its resistance to damage during sterilization if the instrument is to be a multi-use instrument;

(e) the elimination of any danger to a patient caused by an infection through the subsequent use of a medical instrument which may still be contaminated, in that the reduction in the cost thereof renders the device disposable as a "throw-away" after a single use, while nevertheless being appreciably more cost effective in contrast with the currently used medical instruments.

Although the description above contains many specificities, these should not be construed as limiting the scope of the invention but as merely providing illustrations of some of the presently preferred embodiments of this invention. Various other embodiments and ramifications are possible within the scope of the invention. For example, the handle can have other shapes and grasping arrangements that would also be ergonomic and simple to produce in a basic molding or casting process. As another example, palm blocking arch 14 could take the form of a pointed or peaked arch, and thumb ring 20 could take a variety of forms, such as a plunger rather than a ring, or could be surmounted with a burr, spike, or similar clear and obvious visual deterrent against applying one's palm to the thumb ring. Also, various means for anchoring the instrument end effector drive wire or wires can be contemplated. Additionally, while polyethylene or polycarbonate have been suggested as materials, other materials could be employed for all parts.

Thus the scope of the invention should be determined by the appended claims and their legal equivalents, rather than by the examples given.

What is claimed is:

1. In an ergonomic handle for medical instruments of the type comprising a main handle body with a means for grasping and a thumb engaging member slidably mounted to said main handle body, the improvement wherein said main handle body has an integral member of predetermined shape for preventing an operator from applying the heel or palm of his or her hand to said thumb engaging member.

2. The handle of claim 1 wherein said main handle body has at its distal end contoured finger grasping members.

3. The handle of claim 1 wherein said main handle body has a longitudinal channel which is located medially and axially and which is of a predetermined cross-sectional shape, and which extends from said main handle body's distal end to a point at which said integral member extends from said main handle body.

4. The handle of claim 3 wherein said channel permits for placement of an anchor point for an end effector drive wire or drive wires.

5. The handle of claim 3 wherein an assembly hole permits for access to said channel.

6. The handle of claim 1 wherein said thumb engaging member is elongated and has as its proximal end a member for receiving the thumb and at its distal end a lumen for receiving an end effector driving element or elements and having along a section of said trigger member a slot of predetermined shape permitting for slidable longitudinal reciprocating motion about a point of attachment of an instrument end effector driving element or elements.

7. In a medical instrument handle of the type comprising a handle, and a triggering mechanism slidably mounted to the handle, the improvement comprising:

a palm blocking member integral with the handle and preventing the palm of the hand from contacting the triggering mechanism.

* * * * *